US008034229B2

(12) United States Patent
Zhou et al.

(10) Patent No.: US 8,034,229 B2
(45) Date of Patent: *Oct. 11, 2011

(54) PROCESS FOR CATHODIC PROTECTION OF ELECTRODE MATERIAL

(75) Inventors: Dao Min Zhou, Saugus, CA (US); Amy Hines, Monterey Park, CA (US); James Singleton Little, Saugus, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/708,358

(22) Filed: Feb. 18, 2010

(65) Prior Publication Data
US 2010/0147702 A1   Jun. 17, 2010

Related U.S. Application Data

(62) Division of application No. 11/881,254, filed on Jul. 26, 2007, now Pat. No. 7,691,252.

(60) Provisional application No. 60/833,330, filed on Jul. 26, 2006.

(51) Int. Cl.
*C23F 13/04* (2006.01)

(52) U.S. Cl. ........ 205/740; 205/724; 205/725; 205/726; 205/727

(58) Field of Classification Search .................. 205/740, 205/724, 725, 726, 727; 128/897; 600/300
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,189,536 | B1 * | 2/2001 | Martinez et al. ............... 128/897 |
| 6,400,989 | B1 | 6/2002 | Eckmiller |
| 6,458,157 | B1 | 10/2002 | Suaning |
| 6,974,533 | B2 | 12/2005 | Zhou |
| 7,181,287 | B2 | 2/2007 | Greenberg |
| 7,638,032 | B2 * | 12/2009 | Zhou et al. ............... 205/740 |
| 7,691,252 | B2 * | 4/2010 | Zhou et al. ............... 205/740 |
| 2002/0111658 | A1 | 8/2002 | Greenberg et al. |
| 2002/0123780 | A1 | 9/2002 | Grill et al. |
| 2003/0195601 | A1 | 10/2003 | Hung et al. |
| 2003/0236557 | A1 | 12/2003 | Whitehurst et al. |
| 2004/0220652 | A1 | 11/2004 | Zhou et al. |
| 2005/0271895 | A1 | 12/2005 | Zhou |
| 2006/0063062 | A1 | 3/2006 | Zhou et al. |
| 2006/0247754 | A1 | 11/2006 | Greenberg et al. |
| 2006/0259108 | A1 | 11/2006 | Hung et al. |
| 2006/0259109 | A1 | 11/2006 | Zhou et al. |
| 2006/0259112 | A1 | 11/2006 | Greenberg et al. |
| 2007/0089992 | A1 | 4/2007 | Zhou |
| 2007/0092786 | A1 | 4/2007 | Zhou |
| 2007/0191911 | A1 | 8/2007 | Greenberg et al. |

FOREIGN PATENT DOCUMENTS

GB    2 301 840 A    12/1996

OTHER PUBLICATIONS

Eugene De Juan, Retinal Tacks, American Journal of Ophthalmology 99: pp. 272-274, Mar. 1995.

* cited by examiner

*Primary Examiner* — Bruce Bell
(74) *Attorney, Agent, or Firm* — Scott B Dunbar; Gary Schnittgrund; Tomas Lendvai

(57) ABSTRACT

The invention is a process for cathodic protection of electrodes wherein negative bias is applied on the electrode. The negative bias is obtained by asymmetric current pulse, which is obtained by negative phase pulsing with higher amplitude than that of the anodic phase. The asymmetric current pulse is obtained by negative phase pulsing with wider pulse width than that of the anodic phase. The asymmetric current pulse may also be obtained by negative phase pulsing with both higher amplitude and wider pulse width than that of the anodic phase. The invention further relates to a process for cathodic protection of electrodes, wherein negative bias is applied on the electrode, and the negative bias is obtained by asymmetric current pulse, where the asymmetric current pulse is obtained by negative phase pulsing with wider pulse width than that of the anodic phase. The wider pulse width is obtained by pulse trains.

9 Claims, 10 Drawing Sheets

PROCESS FOR CATHODIC PROTECTION OF ELECTRODE MATERIAL

CROSS-REFERENCE TO RELATED APPLICATIONS

This application is a division of U.S. patent application Ser. No. 11/881,254, filed Jul. 26, 2007, now U.S. Pat. No. 7,691,252 which claims the benefit of U.S. Provisional Application No. 60/833,330, filed Jul. 26, 2006 and the benefit of U.S. Provisional Application No. 60/833,386, filed Jul. 26, 2006, the disclosure of all of which is hereby incorporated by reference.

FEDERALLY SPONSORED RESEARCH

This invention was made with government support under grant No. R24EY12893-01, awarded by the National Institutes of Health. The Government has certain rights in the invention.

FIELD OF THE INVENTION

The field of the invention relates to cathodic protection for electrode materials prone to corrosion including oxidation and anodic dissolution.

DESCRIPTION OF RELATED ART

Platinum has often been used as a material for electrodes in corrosive environments such as the human body due to its superior electrical characteristics, biocompatibility and stability. Platinum has many desirable qualities for use as an electrode for electrical stimulation of body tissue. Since platinum has a smooth surface and its surface area is limited by the geometry of the electrode, it is not efficient for transferring electrical charge. The platinum with a smooth surface is hereinafter called "shiny platinum".

Electrodes for stimulating body tissue by electrical stimulation are known in great variety. For the utility of an implantable stimulation or sensing electrode—especially one intended for long-term use in a tissue stimulator with a non-renewable energy source and that, therefore, must require minimal energy—a high electrode capacitance and correspondingly low electrical impedance is of great importance. Furthermore, without sufficiently low impedance, a large voltage may cause polarization of both the electrode and the tissue to which the electrode is attached forming possibly harmful byproducts, degrading the electrode and damaging the tissue.

Because the ability of an electrode to transfer current is proportional to the surface area of the electrode and because small electrodes are necessary to create a precise signal to stimulate a single nerve or small group of nerves, many in the art have attempted to improve the ability of an electrode to transfer charge by increasing the surface area of the electrode without increasing the size of the electrode.

One approach to increase the surface area of a platinum electrode without increasing the electrode size and therefore to improve the ability of the electrode to transfer charge is to electroplate platinum rapidly such that the platinum molecules do not have time to arrange into a smooth, shiny surface. The rapid electroplating forms a platinum surface which is commonly known as "platinum black". Platinum black has a porous and rough surface which is less dense and less reflective than shiny platinum. U.S. Pat. No. 4,240,878 to Carter describes a method of plating platinum black on tantalum.

Platinum black is more porous and less dense than shiny platinum. Platinum black has weak structural and physical strength and is therefore not suitable for applications where the electrode is subject to even minimal physical stresses. Platinum black also requires additives such as lead to promote rapid plating. Lead, however, is a neurotoxin and cannot be used in biological systems. Finally, due to platinum black's weak structure, the plating thickness is quite limited. Thick layers of platinum black simply fall apart.

For the foregoing reasons there is a need for an improved platinum surface coating and process for electroplating the surface to obtain an increased surface area for a given geometry and at the same time the coating is structurally strong enough to be used in applications where the platinum surface coating is subject to physical stresses.

Titanium nitride (TiN) coating has been widely used as biomaterials for orthopedic prostheses, cardiac valves and as electrode materials for sensing and charge-injecting electrodes [1,2]. Titanium nitride (TiN) offers several advantages including higher surface area providing by its columnar structure and capacitive charge-injection process. However, it was found that TiN can be passivated at a higher anodic voltage. The reaction of electrochemically passivation of TiN surface is irreversible. The resulting surface is less conductive. EDX [where "EDX" stands for Energy Dispersive X-ray analysis. It is sometimes referred to also as EDS or EDAX analysis. It is a technique used for identifying the elemental composition of a specimen, or an area of interest.] results confirm that passivated TiN surface is oxygen rich. See M. Janders, U. Egert, M. Stelzle, and W. Nisch, "Novel Thin Film Titanium Nitride Micro-electrodes with Excellent Charge Transfer Capability for Cell Stimulation and Sensing Applications," 18th Annual international Conference of the IEEE Engineering in Medicine and Biology Society, Amsterdam, pp. 245-247, 1996. M. Schaldach, M. Hubmann, A. Weikl, and R. Hardt, "Sputter-deposited TiN electrode coatings for superior sensing and pacing performance", Pace, vol. 3, pp. 1891-1895, 1990. S. Logothetidis, E.-I. Meletis, G. Stergioudis, and A.-A. Adjattor, "Room temperature oxidation behavior of TiN thin films," Thin Solid films, vol. 336, pp 304-313, 1999. D. Zhou and R. Greenberg, "Tantalum Capacitive Microelectrode Array for a Neural Prosthesis" in Chemical and Biological Sensors and Analytical Methods II, (eds., M. Butler, P. Vanysek. and N. Yamazoe, pp. 622-629, 2001.

BRIEF SUMMARY OF INVENTION

The present invention is directed cathodic protection for electrode materials prone to corrosion including oxidation and anodic dissolution. Metal electrode materials including noble metal, such as Pt will suffer from metal oxidation and dissolution during stimulation even by a charge balanced waveform within water window potentials. The metal dissolution not only causes the damage of electrodes, but also affects the biological tissue surfaces. This limits the lifetime of the medical implants for chronic applications.

Application of negative bias on stimulation electrodes, to prevent the anodic voltage excursion exceed +1.3V. The negative bias can be created by an asymmetric current pulse (negative phase has a higher amplitude and/or wider pulse width than that of anodic phase) or a negative DC bias. To avoid pH increase due to water reduction, the negative bias should be limited to keep the voltage excursion within the water window. Alternatively, TiN can be used for monophasic pulse as

DETAILED DESCRIPTION OF THE INVENTION

Metal electrode materials including noble metal, such as Pt, will suffer from metal oxidation and dissolution during stimulation even by a charge balanced waveform within water window potentials. The metal dissolution not only causes the damage of electrodes, but also affects the biological tissue surfaces. This limits the lifetime of the medical implants for chronic applications.

Applying a negative bias on the stimulation electrodes prevents the anodic voltage excursion from exceeding +1.3V. This negative bias is created by an asymmetric current pulse (the negative phase has a higher amplitude and/or a wider pulse width than that of the anodic phase) or a negative DC bias. To avoid a pH increase due to water reduction, the negative bias is limited to keep the voltage excursion within the water window. Alternatively, TiN can be used for monophasic pulse as a cathode only. This method is also useful for other electrode materials, like Pt, Pd, Ti, TiN, Nb, Rh, Ir, Au, or W.

The tests results show that TiN prone to oxidation and it will limit its usage for long term stimulation application.

Figure 1:
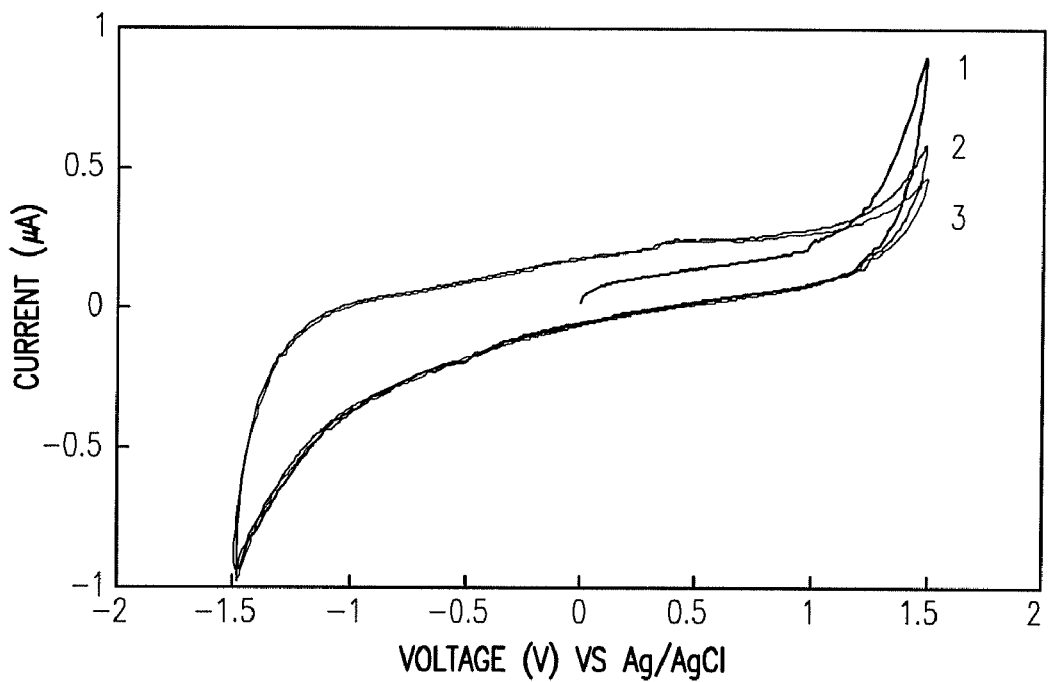
FIG. 1 shows a typical cyclic voltammogram of a TiN electrode.

FIG. 1 shows a typical cyclic voltammogram of a TiN electrode. FIG. 1 shows more specifically cyclic voltammograms of a TiN electrode at a potential scan rate of 100 mV/sec.

No visible oxidation/reduction peaks occur within the water window of +/−1V. This suggests that if pulsed within water window, charge injection of TiN is through non-faradic processes, i.e. mainly via a capacitive mechanism. At the voltage higher than −1V, the sharp increase in cathodic current is due to the hydrogen evaluation. At the voltage higher than +1V, the anodic current decreases with continuous potential scan. There is no gas evolution observed. This indicates that the TiN surface is passivated at the potential higher than +1V, instead of oxygen evolution reaction. Multiple cyclic voltammetry (CV) measurements repeated on same TiN samples show that the reduced anodic current can't be recovered and this suggests that the passivation reaction is irreversible.

Figure 2:
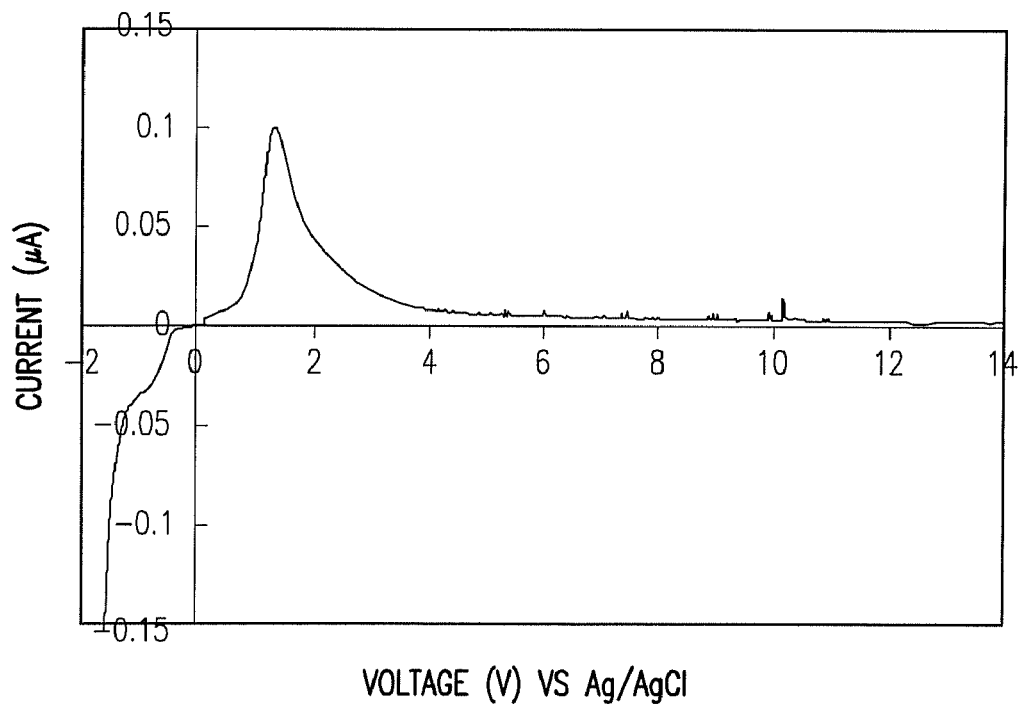
FIG. 2 shows a linear polarization curve of a TiN electrode at a potential scan rate of 5 mV/sec.

Linear polarization curves were measured to confirm TiN passivation observed in CV measurements and determine passivation potential at anodic voltage range as shown in FIG. 2. FIG. 2 shows more specifically linear polarization curve of a TiN electrode at a potential scan rate of 5 mV/sec.

The cathodic curve was scanned from open circuit potential to −2V while anodic curve was scanned from open circuit potential to +14V at a slow scan rate of 5 mV/sec. The predominate passivation peak at anodic scan phase was observed for all the TiN electrodes measured. It was found that the passivation starts from about +1.3V which is in agreement with the results from CV measurements. At the voltage higher than +3V, the TiN is totally passivated.

Figure 3:
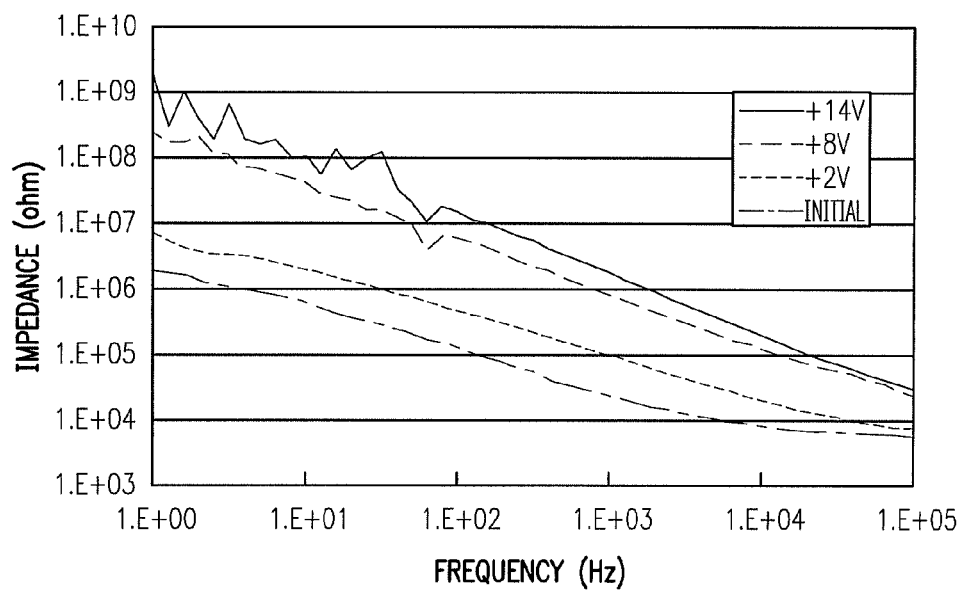
FIG. 3 shows Bode plots of a TiN electrode passivated with various anodic voltages. EIS were measured at AC 10 mV with no DC bias.

EIS measurements were conducted at open circuit potential with a 10 mV AC excitation potential. The frequency was scanned from 100 kHz to 1 Hz. The impedance changes with passivation voltage are shown in FIG. 3. FIG. 3 presents Bode plots of a TiN electrode passivated with various anodic voltages. EIS were measured at AC 10 mV with no DC bias.

The electrode impedance increased dramatically while the passivation voltage increased from 2V to 14V. The electrode impedance at 1000 Hz is increased from initially 20 kohm to 1800 kohm at +14V. EIS measurements also confirmed that the passivated TiN can not been reduced by applied a cathodic voltage or cathodic current pulse.

Figure 4:
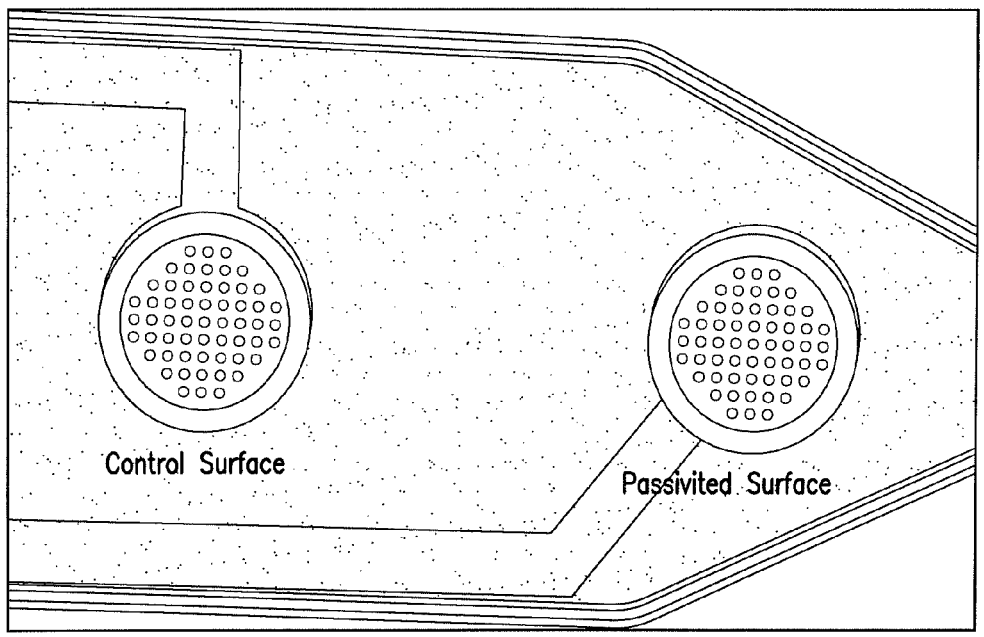
FIG. 4 shows an optical microscopic image shows darker TiN surface after anodically biased at a voltage above +1.5V.

The passivated TiN surface has a darker brown color in comparison to its control surface, as shown in FIG. 4. This darken surface appears brittle and has a poor adhesion to the Si substrate. FIG. 4 shows more specifically an optical microscopic image shows darker TiN surface after anodically biased at a voltage above +1.5V.

EDX examinations were carried out to compare surface elements changes before and after TiN passivation. For the TiN surface before passivation, a roughly Ti:N ratio of 1:1 is detected. However, after passivation, increased oxygen content was detected. The higher the passivation voltage, the higher the oxygen content on TiN surface. This suggested that passivation will result in the replacement of nitrogen by oxygen, i.e. oxidation of TiN to $TiO_x$. For some TiN surface anodically biased to higher than +5V, a Ti:O ratio of 1:2 was detected, indicating formation of $TiO_2$. The oxidation of TiN may be due to its void boundaries of columnar structure providing an easy oxygen diffusion path or due to over stoichiometry of TiN with loosely bound nitrogen to titanium being prone to oxidation.

Figure 5A:
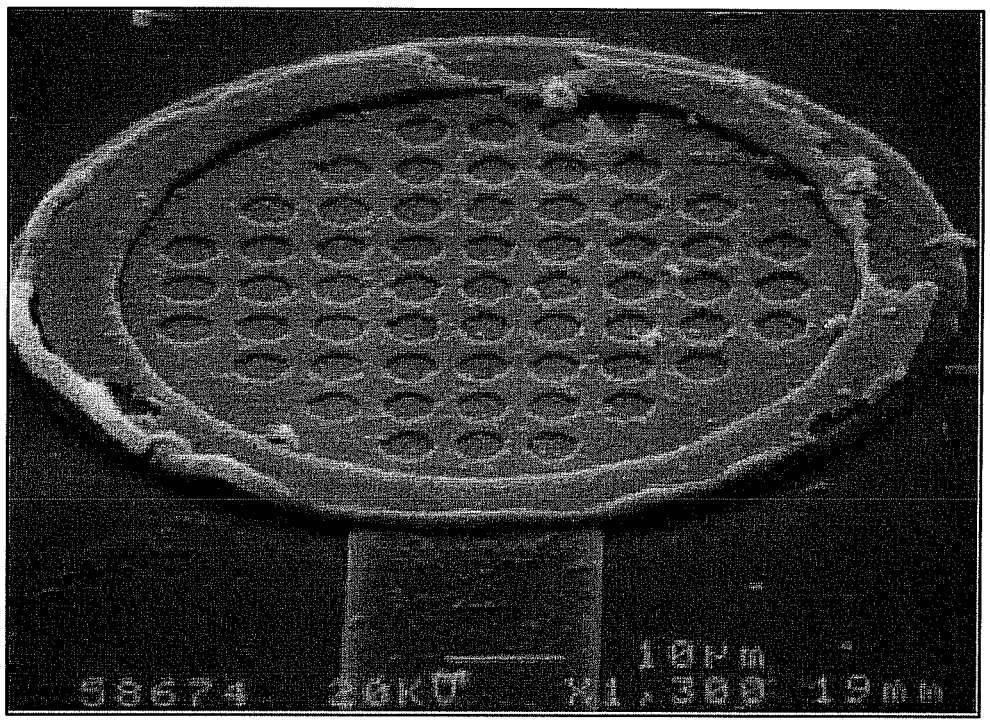
FIG. 5 shows SEM micrograph (5a) a partially (at edge) delaminated and (5b) totally damaged TiN surfaces.
Figure 5B:
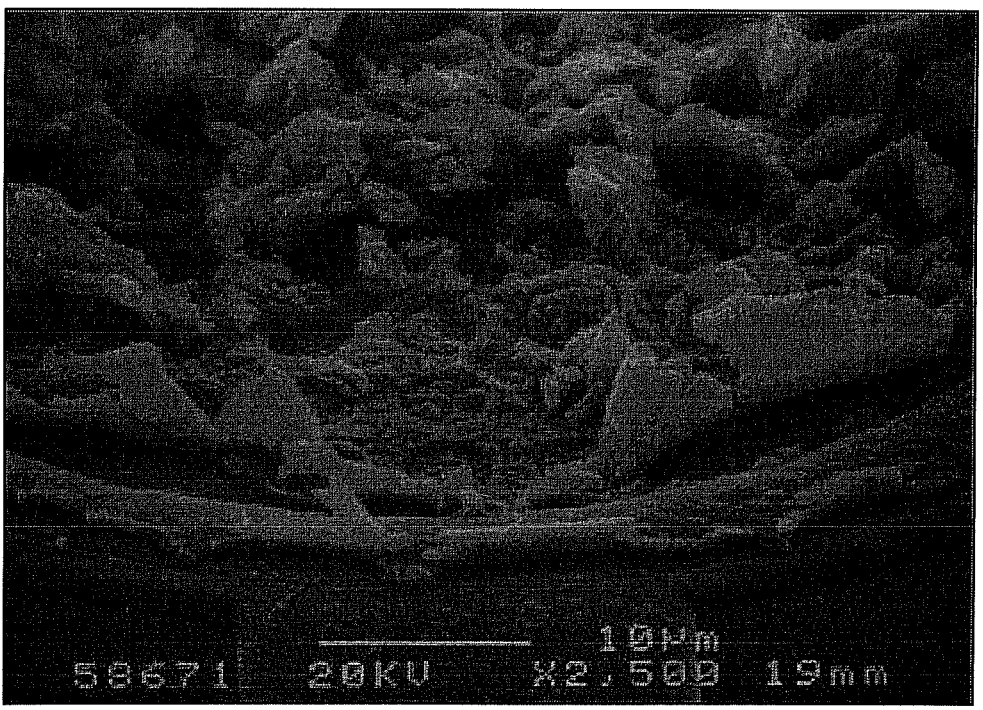

Gentle gassing of the TiN electrode surface generated by cathodic voltage bias did not damage the electrode in terms of injectable charge (Qinj) and adhesion. However, if the surface is passivated, Qinj is lost and gassing generated on the electrode surface will damage the TiN coating. FIGS. 5(a) and (b) show a slightly damaged and a total damaged TiN surface due to gassing on the passivated surfaces. SEM photomicrographs (FIGS. 5(a) and 5(b)) show (a) a partially at edge delaminated and (b) damaged TiN surfaces.

Metal electrode materials including noble metal, such as Pt, will suffer from metal oxidation and dissolution during stimulation even by a charge balanced waveform within water window potentials. The metal dissolution not only causes the damage of electrodes, but also affects the biological tissue surfaces. This limits the lifetime of the medical implants for chronic applications.

Figure 6A:
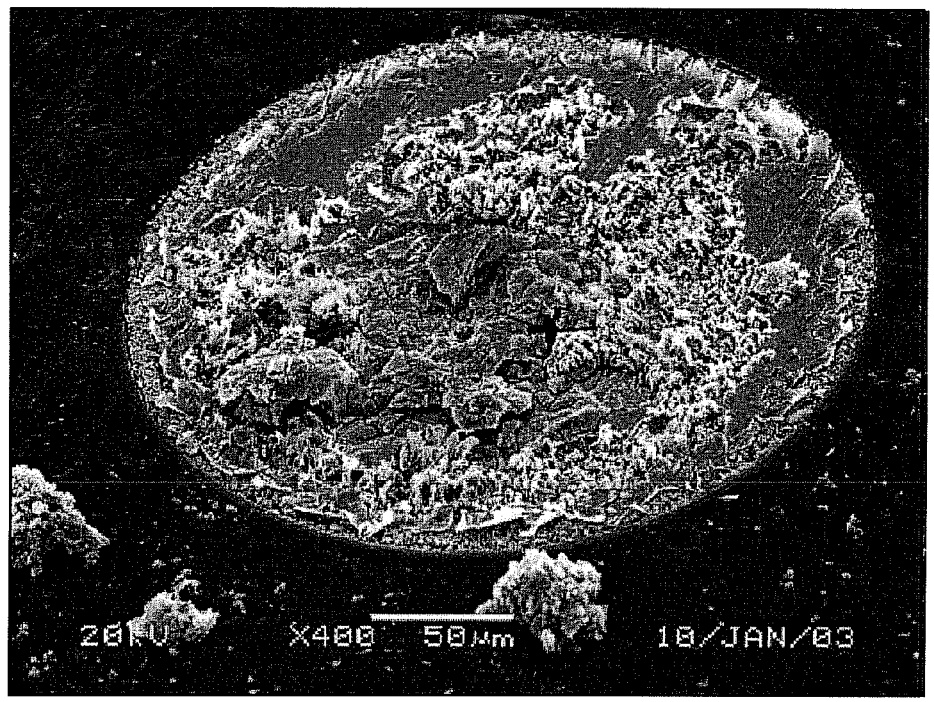
FIG. 6 shows a corroded Pt electrode surface (FIG. 6a) due to both Pt dissolution and Pt oxidation pulsed by a charge balanced waveform in comparison to a control surface (FIG. 6b).
Figure 6B:
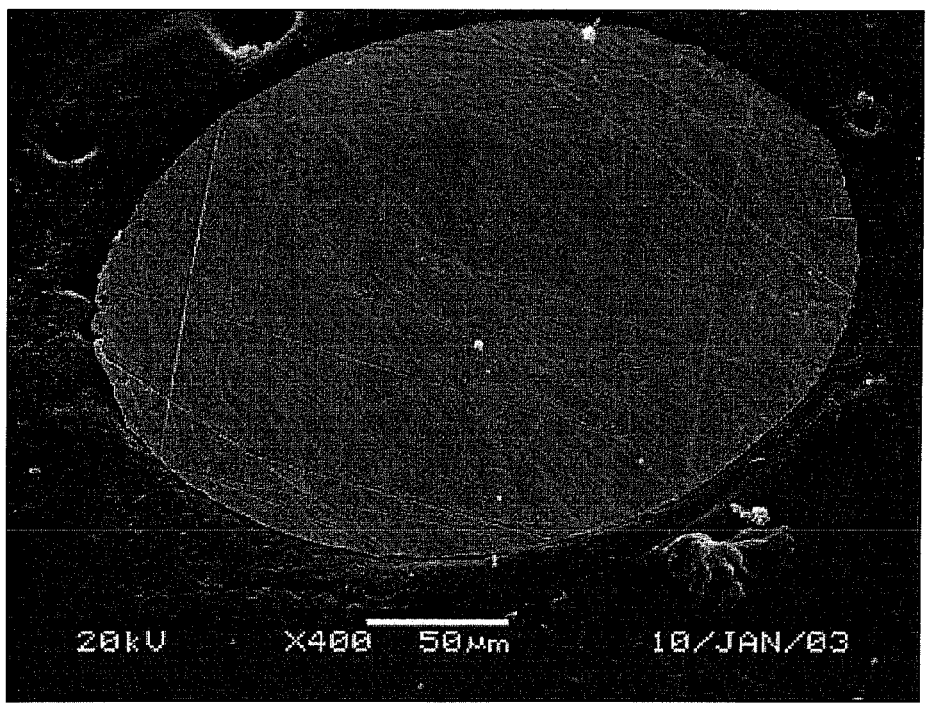

FIG. 6 shows a corroded Pt electrode surface (FIG. 6a) due to both Pt dissolution and Pt oxidation pulsed by a charge balanced waveform in comparison to a control surface (FIG. 6b).

Metal oxidation and dissolution are anodic electrochemical reactions. During pulse stimulation, metal dissolution occurs at the anodic phase when the electrode voltage is positive against the return electrode. The positive voltage remains on the electrode after the anodic pulse completed and decades as the built-up charge disperses. Using cathodic first charge balanced waveform will pull the electrode voltage towards negative direction, the metal oxidation and dissolution will be naturally reduced. More effectively, by applying a negative bias on the electrode, the metal dissolution can be minimized or prevented depending on the degree of the biases. The negative bias will keep the anodic voltage as low as possible or the period of anodic voltage to which electrode subjected as short as possible. To avoid pH increase due to water reduction, the negative bias should be limited to keep the voltage excursion within the water window.

The negative bias is created by a charge unbalanced waveform or by a dc current. One example of such waveform is the one with larger negative current amplitude than that of the anodic current for the pulses with same pulse width. The other example is that a wider negative pulse than that of the anodic pulse with same current amplitudes. The third example is the combination of above examples: a wider and a larger negative pulse than that of anodic pulse. This method is also useful for other electrode materials, like Pt, Pd, Ti, TiN, Nb, Rh, Ir, Au, or W.

The tests results (see Table 1 and FIGS. 7-14) show that positive biased pulses cause severe corrosion of the Pt electrode while the negatively biased pulse protected the electrode surface. The corrosion of Pt electrodes is measured as the metal dissolution and metal oxidation.

Figure 7:
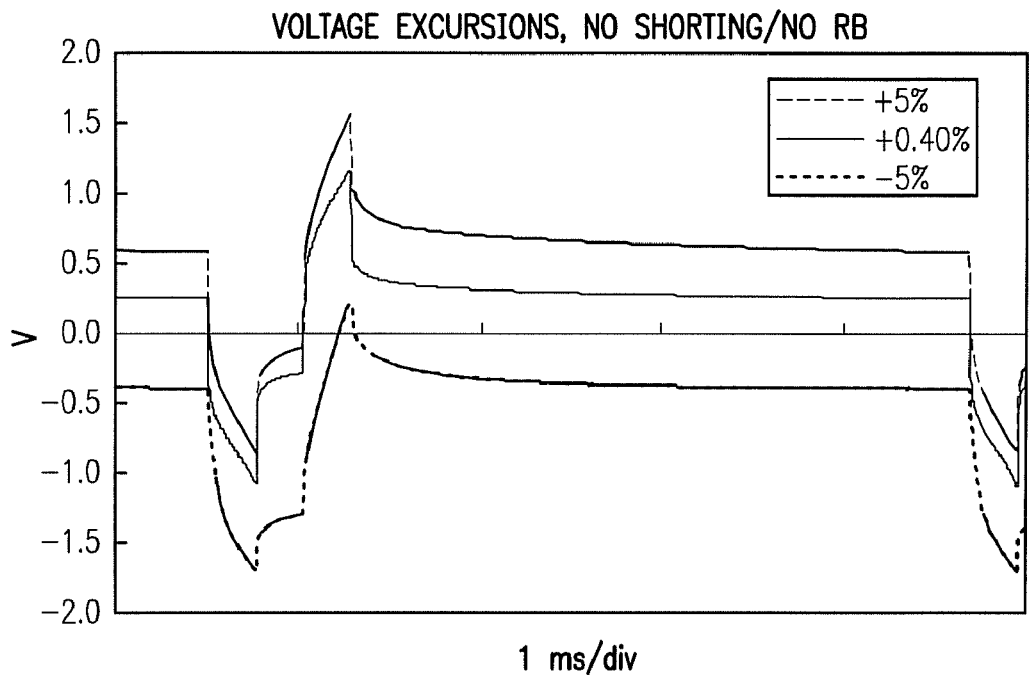
FIG. 7 shows a comparison of Voltage excursions for various unbalanced pulse waveforms.

FIG. 7 presents a comparison of voltage excursions for various unbalanced pulse waveforms. Negatively biased waveform causes the electrode voltage shifted towards negative direction and provide a cathodic protection for Pt dissolution and oxidation.

Figure 8:
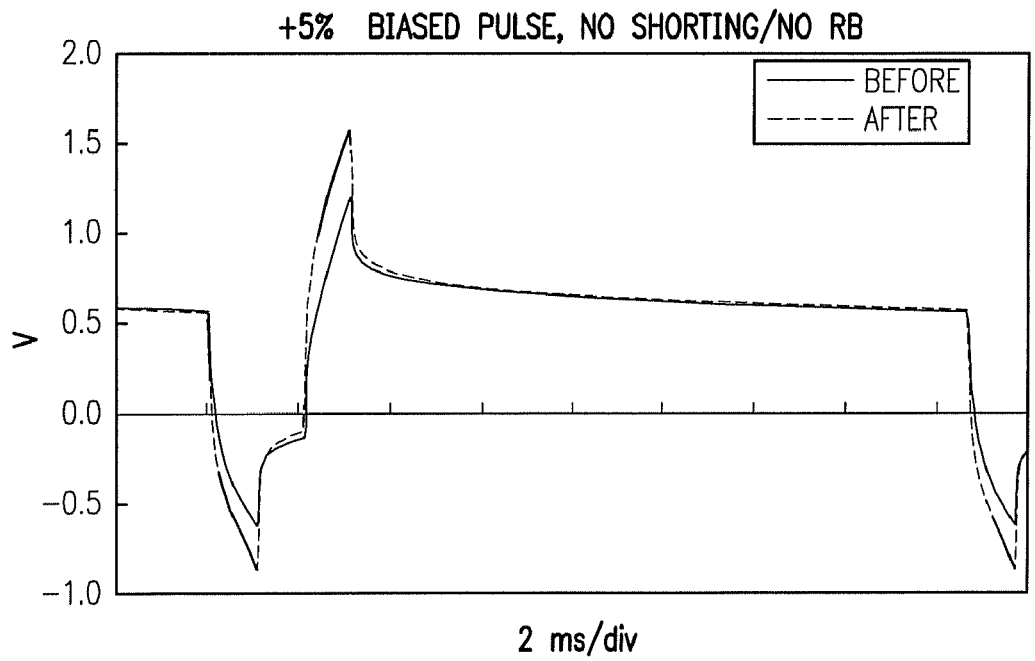
FIG. 8 shows an excursion change after 6 hour pulse stimulation for a +5% biased pulse.

FIG. 8 presents voltage excursion changes after 6 hour pulse stimulation for a +5% biased pulse. The electrode voltage increased after Pt surface oxidation. Pt oxide is less conductive than Pt.

Figure 9:
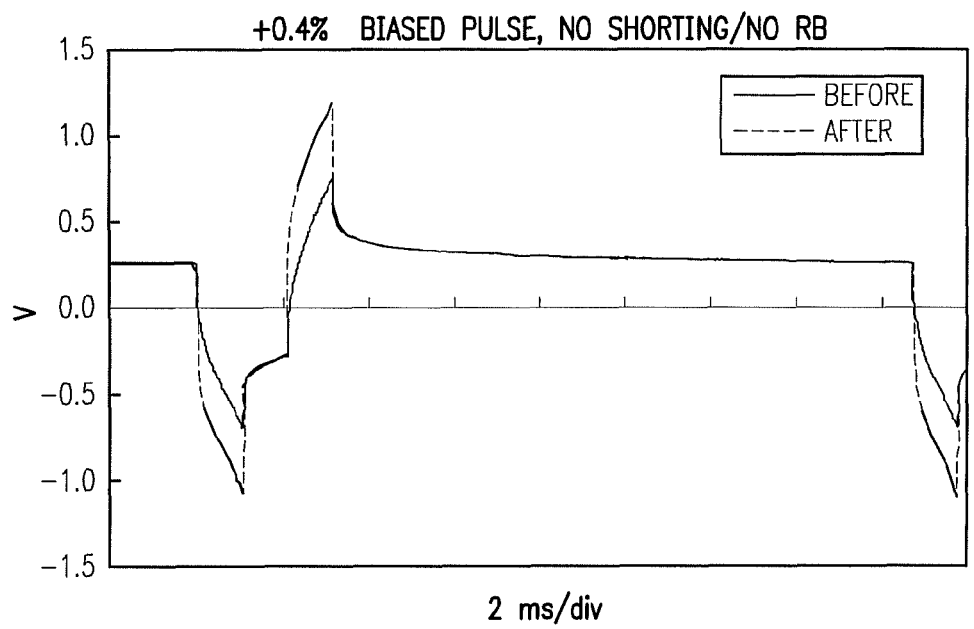
FIG. 9 shows a voltage excursion changes after unbalanced pulse (+0.4%) stimulation for 6 hours.

FIG. 9 presents voltage excursion changes after unbalanced pulse (+0.4%) stimulation for 6 hours. The voltage increase is due to Pt surface oxidation.

Figure 10:
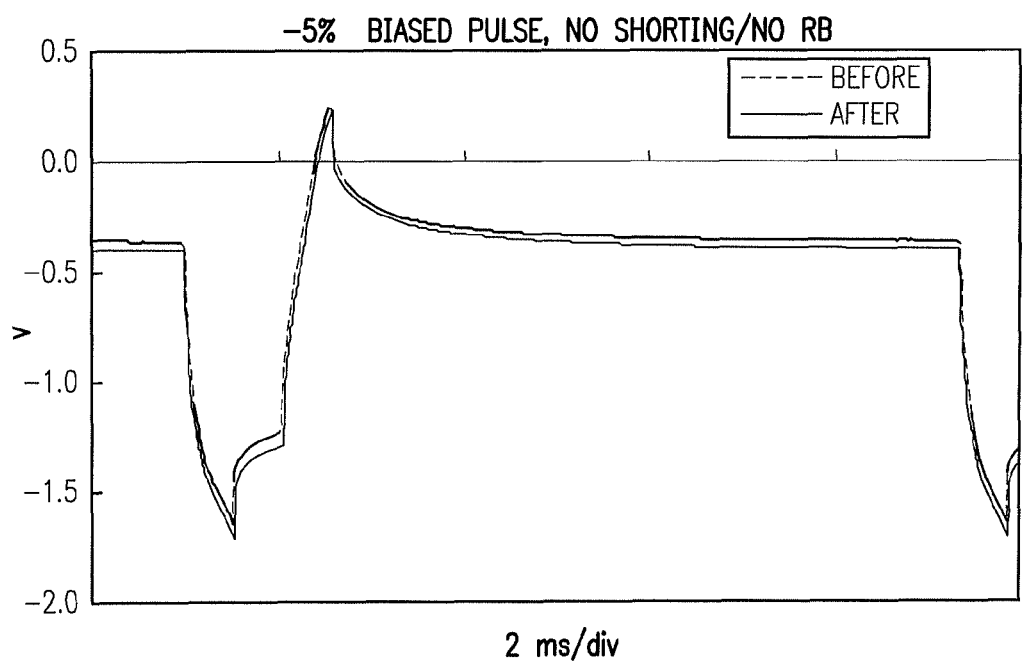
FIG. 10 shows a voltage excursion change after −5% negatively biased waveform pulse stimulation for 6 hours.

FIG. 10 presents voltage excursion changes after −5% negatively biased waveform pulse stimulation for 6 hours. No significant voltage changes after stimulation indicates minimal surface changes.

Figure 11A:
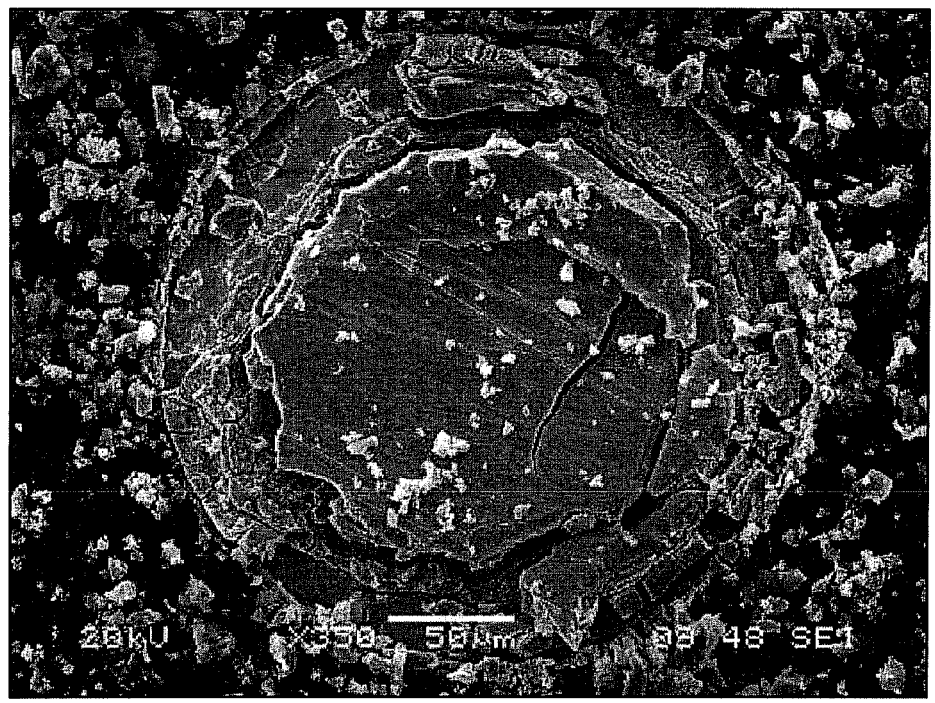
FIG. 11 shows two typical surface images after 6 hour positively biased (+5%) waveform pulse stimulation.
Figure 11B:
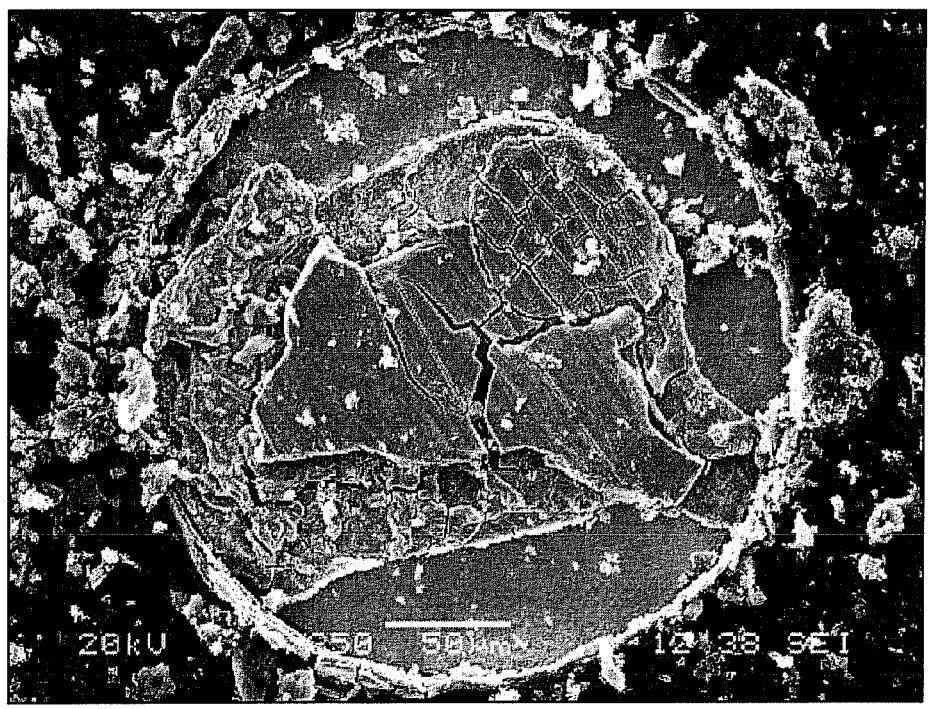

FIG. 11 presents two typical surface images after 6 hours positively biased (+5%) waveform pulse stimulation.

Figure 12A:
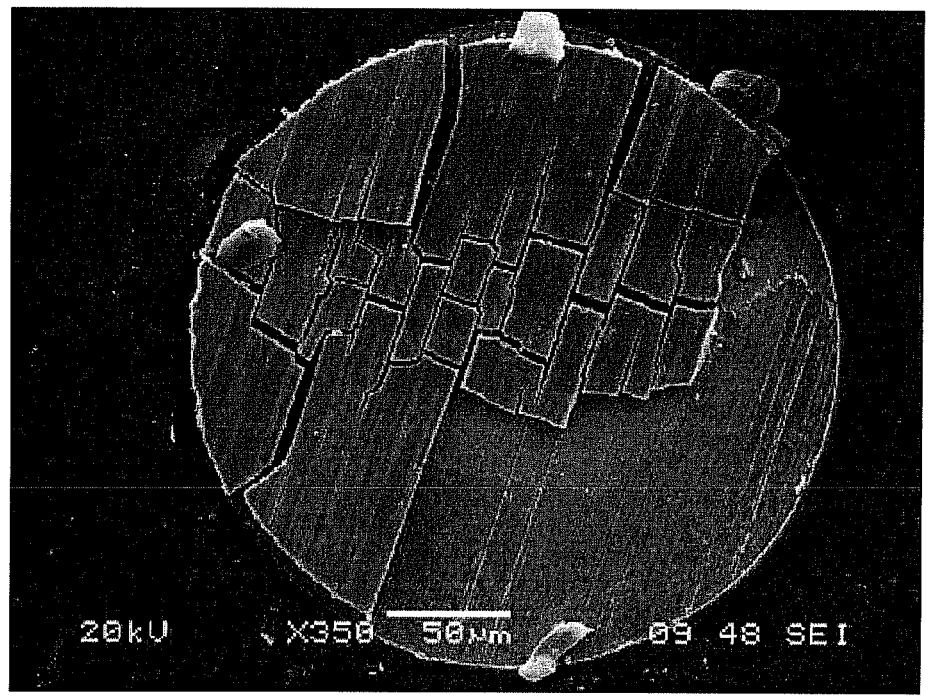
FIG. 12 shows two typical electrode surfaces after 6 hour +0.4% biased waveform pulse stimulation.
Figure 12B:
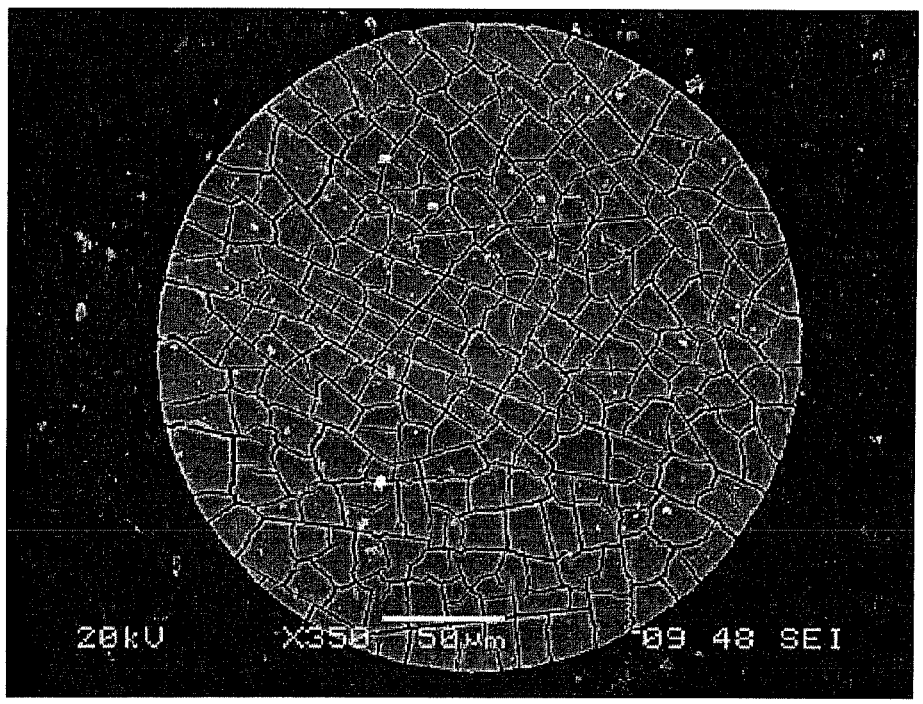

FIG. 12 presents two typical electrode surfaces after 6 hours +0.4% biased waveform pulse stimulation.

Figure 13A:
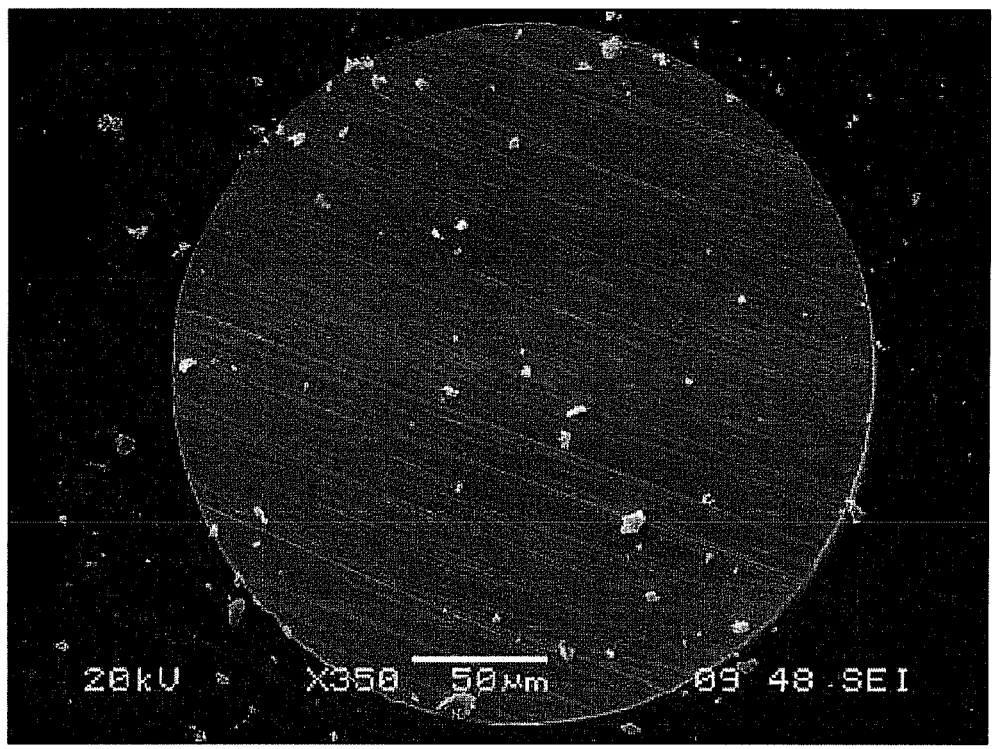
FIG. 13 shows two typical electrode surfaces after 6 hour −5% biased waveform pulse stimulation.
Figure 13B:
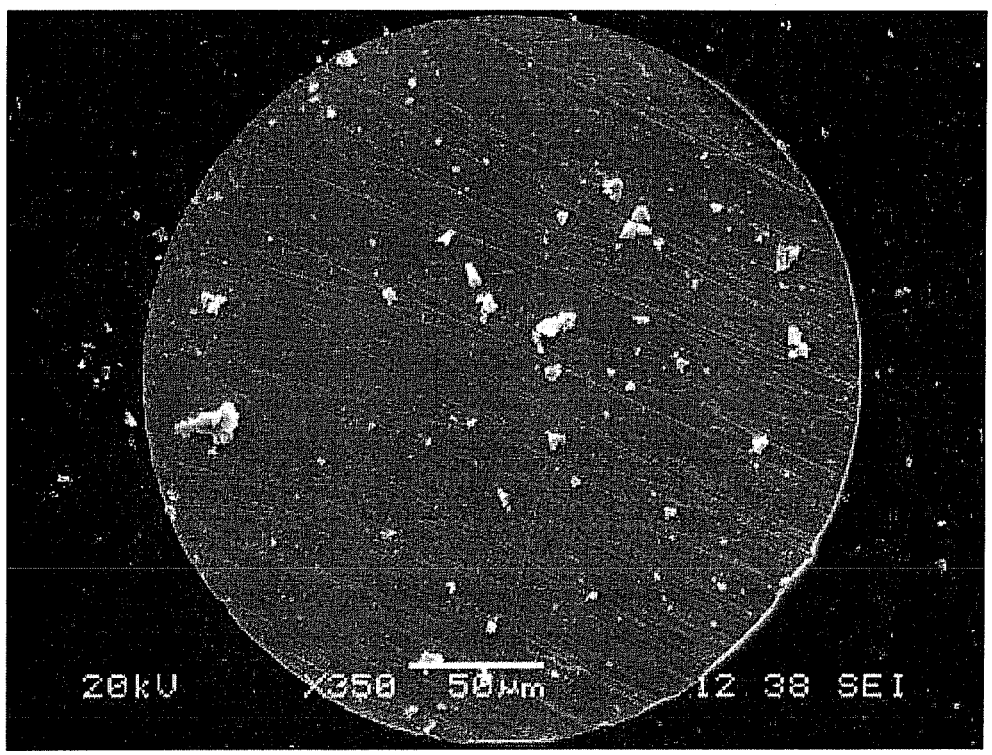

FIG. 13 presents two typical electrode surfaces after 6 hours −5% biased waveform pulse stimulation. The electrode surface presents no change after 6 hours stimulation.

Figure 14A:
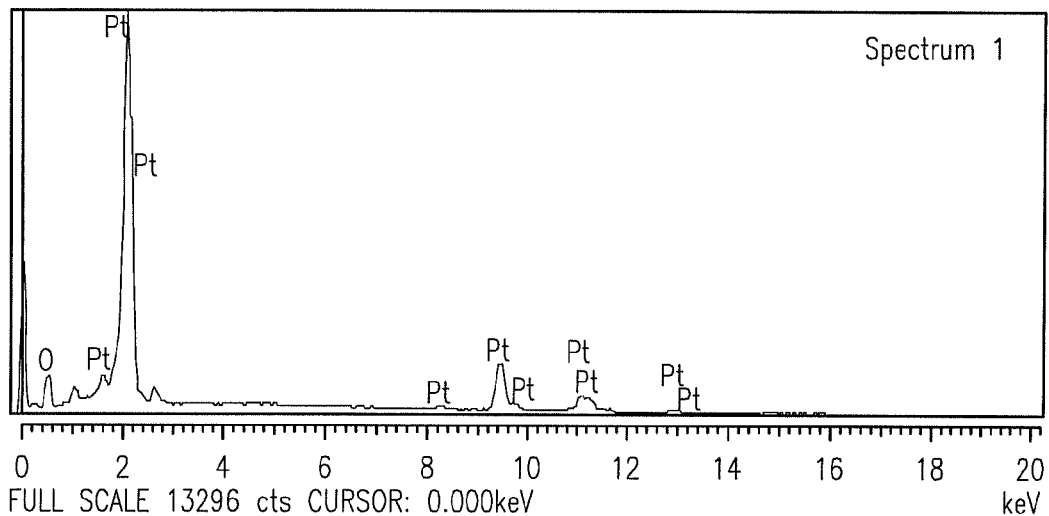
FIG. 14 shows an EDX spectrum for an electrode surface pulsed by a +5% biased waveform (FIG. 14a). Oxygen peak is detected, indicated Pt surface oxidation after pulsing (FIG. 14b).
Figure 14B:
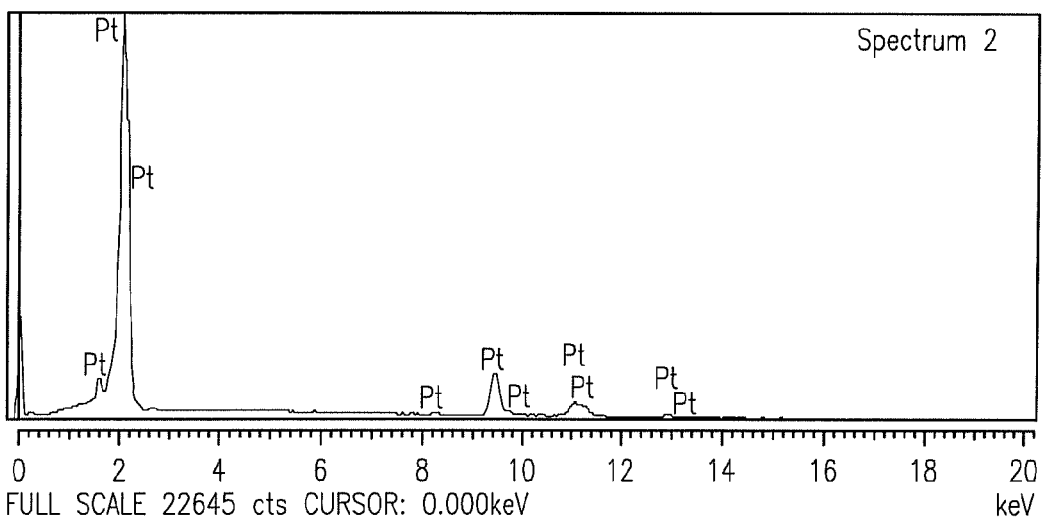

FIG. 14 presents an EDX spectrum for an electrode surface pulsed by a +5% biased waveform (FIG. 14a). An oxygen peak is detected, indicating that Pt surface oxidation after pulsing has occurred. EDX spectrum for an electrode surface pulsed by a −5% biased waveform are presented in FIG. 14b. No oxygen peak is detected, indicating that a negative biased waveform prevented Pt surface oxidation. While a −5% biased waveform is preferred the negative pulses may provide greater charge from 1-15%; greater charge from 3-7%; or greater charge from 4-6%.

Table 1 below contains EDX, ICP-MS and EIS results for electrodes pulsed by various biased waveforms. All electrodes have a 250 um diameter and a polished Pt surface as the electrode surface. The pulse has a 1 ms pulse width at 60 Hz and a charge density of 0.35 mC/cm$^2$.

TABLE 1

| Electrode arrays | Bias Condition | Oxygen Concentration from Edx (atomic %) | Pt in test solution by ICP-MS (ppm)* | Series Resistance Rs (ohm) Average initial Rs = 1378 ohm |
|---|---|---|---|---|
| #199 | +5% | 67% | 0.67 | 2840 |
| 200 | +5% |  | 0.42 | 2899 |
| 203 | +0.4%, no bias | 67% | 0.0071 | 4490 |
| 204 | +0.4%, no bias |  | 0.0070 | 4215 |
| 201 | −0.5% | 0% | 0.0008 | 1341 |
| 157 | −0.5% |  | 0.0010 | 1477 |

*ICP-MS detection limit: 0.00002 ppm. Measured in 10 ml solution, pulsed 6 hr with 5 250 um electrodes.

Table 2 shows the results of a chip long-term stimulation, platinum grey (PtG) chip long-term stimulation, 4 groups/4 arrays per group/5 electrodes per array, pulsed by a chip at 0.35 mC/cm$^2$, 1-1-1 ms (where this is 1 ms cathodic, 1 ms interface delay, and 1 ms anodic), 60 Hz, shorting for 2 ms at 11 ms if any, 10 mM phosphate buffer solution (PBS) at 37° C., large Pt common electrode, Pt grey on thin-film/polyimide arrays, 200 um diameter

TABLE 2

| Array | Array ID | # of E | Days | Observations |
|---|---|---|---|---|
| Anodic Bias-no Shorting(150k Rb/+(3-5)% bias) | | | | |
| 5.2 | ABL07 #8 | 5 | >771 | Increased Rs/Decreased Caps |
| 5.3 | ABN18 #6 | 5 | >771 | Increased Rs/Decreased Caps |
| 5.4 | ABN05 #7 | 5 | >771 | Increased Rs/Decreased Caps |
| Cathodic Bias-no Shorting(150k Rb/−(3-5)% bias) | | | | |
| 8.1 | ABL03 #7 | 5 | >771 | No Significant Change |
| 8.2 | ABM27 #6 | 5 | >771 | |
| 8.3 | ABN17#5 | 5 | >771 | |
| 8.4 | ABN02 #7 | 5 | >771 | |
| Anodic Bias-Shorting(11-2 ms Sh/+(3-5)% bias) | | | | |
| 9.1 | ABL06 #5 | 5 | >771 | No Significant Change |
| 9.2 | ABM27#8 | 5 | >771 | |
| 9.3 | ABN18 #5 | 5 | >771 | |
| 9.4 | ABN05 #6 | 5 | >771 | |
| Cathodic Bias-Shorting(11-2 ms Sh/−(3-5)% bias) | | | | |
| 12.1 | ABM 22 #6 | 5 | >771 | No Significant Change |
| 12.2 | ABL 06 #6 | 5 | >771 | |
| 12.3 | ABN 10 #6 | 5 | >771 | |
| 12.4 | ABL 20 #7 | 5 | >771 | |

While the invention is described in terms of a specific embodiment, other embodiments could readily be adapted by one skilled in the art. Accordingly, the scope of the invention is limited only by the following claims.

What we claim is:

1. A process for cathodic protection of an electrode wherein:

negative and positive asymmetric biphasic current pulse trains with a negative bias are applied to said electrode; and said asymmetric current pulse trains are obtained by performing said negative phase with wider pulse width than that of an anodic phase.

2. The process according to claim 1, wherein said negative bias is obtained by providing more negative current pulses than positive current pulses.

3. The process according to claim 1 wherein said negative pulses provide greater charge from 1-15%.

4. The process according to claim 1 wherein said negative pulses provide greater charge from 3-7%.

5. The process according to claim 1 wherein said negative pulses provide greater charge from 4-6%.

6. The process according to claim 1 wherein said electrodes are comprised of Pt, Pd, Ti, TiN, Nb, Rh, Ir, Au, or W, their oxides or alloys thereof.

7. The process according to claim 1, wherein said electrodes are biocompatible.

8. The process according to claim 1, wherein said electrodes are suitable to stimulate neural tissue.

9. The process according to claim 1, wherein said negative bias is limited to keep a voltage excursion within a water widow.

* * * * *